United States Patent
Baileykobayashi et al.

(10) Patent No.: US 11,230,586 B2
(45) Date of Patent: Jan. 25, 2022

(54) EXOSOME PRODUCTION METHOD

(71) Applicants: TOAGOSEI CO., LTD., Tokyo (JP); University Public Corporation Osaka, Osaka (JP)

(72) Inventors: Nahoko Baileykobayashi, Tsukuba (JP); Tetsuhiko Yoshida, Tsukuba (JP); Ikuhiko Nakase, Sakai (JP)

(73) Assignees: TOAGOSEI CO., LTD, Tokyo (JP); University Public Corporation Osaka, Osaka (JP)

( * ) Notice: Subject to any disclaimer, the term of this patent is extended or adjusted under 35 U.S.C. 154(b) by 87 days.

(21) Appl. No.: 16/743,379

(22) Filed: Jan. 15, 2020

(65) Prior Publication Data
US 2020/0231647 A1 Jul. 23, 2020

(30) Foreign Application Priority Data
Jan. 22, 2019 (JP) .............. JP2019-008474

(51) Int. Cl.
*C07K 14/705* (2006.01)
*C12N 5/09* (2010.01)
(52) U.S. Cl.
CPC .......... *C07K 14/705* (2013.01); *C12N 5/0693* (2013.01)
(58) Field of Classification Search
CPC .............. C07K 14/723; C07K 2319/03; C07K 14/705; C07K 2319/10; C12N 5/0693
See application file for complete search history.

(56) References Cited

U.S. PATENT DOCUMENTS
2018/0010133 A1 1/2018 Li

FOREIGN PATENT DOCUMENTS
JP 2018-64550 4/2018

OTHER PUBLICATIONS

Kajimoto et al, Ongoing activation of sphingosine 1-phosphate receptors mediates maturation of exosomal multivesicular endosomes, Nat. Commun., 2013, pp. 1-13.*
Hoecke et al. EPHA4 is a Disease Modifier of Amyotrophic Lateral Sclerosis in Animal Models and in Humans. *Nature Medicine*, 2012, vol. 18 p. 1418-1422.
Pyne et al. Sphingosine 1-Phosphate and Cancer. *Nature Reviews*, 2010, vol. 10, p. 489-503.

* cited by examiner

*Primary Examiner* — Li N Komatsu
(74) *Attorney, Agent, or Firm* — Occhiuti & Rohlicek LLP

(57) ABSTRACT

The method of producing induced lightweight exosomes (iLE) provided by the present invention includes preparing a cell culture containing prescribed cultured cells; supplying at least once an artificially produced synthetic peptide to the cell culture and culturing the cell culture for a prescribed interval; and obtaining exosomes produced by the cultured cells following culturing. Here, the synthetic peptide is provided with: (1) an exosome-inducing peptide sequence and (2) a CPP sequence, and has a total number of amino acid residues of 100 or less.

7 Claims, 2 Drawing Sheets

Specification includes a Sequence Listing.

SEQUENCE LISTING

<160> NUMBER OF SEQ ID NOS: 20

<210> SEQ ID NO 1

```
<211> LENGTH: 22
<212> TYPE: PRT
<213> ORGANISM: Artificial Sequence
<220> FEATURE:
<223> OTHER INFORMATION: synthetic peptide

<400> SEQUENCE: 1

Phe Ile Gly Asn Leu Ala Leu Ser Asp Leu Leu Ala Gly Val Ala Tyr
1               5                   10                  15

Thr Ala Asn Leu Leu Leu
            20

<210> SEQ ID NO 2
<211> LENGTH: 14
<212> TYPE: PRT
<213> ORGANISM: Artificial Sequence
<220> FEATURE:
<223> OTHER INFORMATION: synthetic peptide

<400> SEQUENCE: 2

Arg Ser Arg Lys Tyr Thr Ser Trp Tyr Val Ala Leu Lys Arg
1               5                   10

<210> SEQ ID NO 3
<211> LENGTH: 18
<212> TYPE: PRT
<213> ORGANISM: Artificial Sequence
<220> FEATURE:
<223> OTHER INFORMATION: synthetic peptide

<400> SEQUENCE: 3

Met Ala Lys Ser Ile Arg Ser Lys His Arg Arg Gln Met Arg Met Met
1               5                   10                  15

Lys Arg

<210> SEQ ID NO 4
<211> LENGTH: 16
<212> TYPE: PRT
<213> ORGANISM: Artificial Sequence
<220> FEATURE:
<223> OTHER INFORMATION: synthetic peptide

<400> SEQUENCE: 4

Met Ala Arg Arg Arg Arg His Arg Gly Pro Arg Arg Pro Arg Pro Pro
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: synthetic peptide

<400> SEQUENCE: 5

Gly Arg Cys Arg Arg Leu Ala Asn Phe Gly Pro Arg Lys Arg Arg Arg
1               5                   10                  15

Arg Arg Arg

<210> SEQ ID NO 6
<211> LENGTH: 16
<212> TYPE: PRT
<213> ORGANISM: Artificial Sequence
<220> FEATURE:
<223> OTHER INFORMATION: synthetic peptide

<400> SEQUENCE: 6
```

Arg Arg Arg Lys Arg Asn Arg Asp Ala Arg Arg Arg Arg Lys Gln
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Met Gln Arg Lys Pro Thr Ile Arg Arg Lys Asn Leu Arg Leu Arg Arg
1               5                   10                  15

Lys

<210> SEQ ID NO 8
<211> LENGTH: 7
<212> TYPE: PRT
<213> ORGANISM: Artificial Sequence
<220> FEATURE:
<223> OTHER INFORMATION: synthetic peptide

<400> SEQUENCE: 8

Ile Met Arg Arg Arg Gly Leu
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic peptide

<400> SEQUENCE: 9

Lys Lys Leu Lys Lys Arg Asn Lys
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Arg Arg Arg Ala Asn Asn Arg Arg Arg
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic peptide

<400> SEQUENCE: 11

Arg Lys Lys Arg Lys Lys Lys
1               5

<210> SEQ ID NO 12
<211> LENGTH: 15
<212> TYPE: PRT
<213> ORGANISM: Artificial Sequence
<220> FEATURE:
<223> OTHER INFORMATION: synthetic peptide

```
<400> SEQUENCE: 12

Lys Arg Lys Gly Lys Leu Lys Asn Lys Gly Ser Lys Arg Lys Lys
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: synthetic peptide

<400> SEQUENCE: 13

Ser Lys Arg Leu Ser Ser Arg Ala Arg Lys Arg Ala Ala Lys Arg Arg
1               5                   10                  15

Leu Gly

<210> SEQ ID NO 14
<211> LENGTH: 14
<212> TYPE: PRT
<213> ORGANISM: Artificial Sequence
<220> FEATURE:
<223> OTHER INFORMATION: synthetic peptide

<400> SEQUENCE: 14

Lys Arg Pro Arg Arg Arg Pro Ser Arg Pro Phe Arg Lys Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: synthetic peptide

<400> SEQUENCE: 15

Lys Lys Arg Thr Leu Arg Lys Asn Asp Arg Lys Lys Arg
1               5                   10

<210> SEQ ID NO 16
<211> LENGTH: 8
<212> TYPE: PRT
<213> ORGANISM: Artificial Sequence
<220> FEATURE:
<223> OTHER INFORMATION: synthetic peptide

<400> SEQUENCE: 16

Trp Arg Arg Gln Ala Arg Phe Lys
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Arg Lys Lys Arg Arg Gln Arg Arg Arg
1               5

<210> SEQ ID NO 18
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 18

Tyr Ala Arg Ala Ala Ala Arg Gln Ala Arg Ala
1               5                   10

<210> SEQ ID NO 19
<211> LENGTH: 18
<212> TYPE: PRT
<213> ORGANISM: Artificial Sequence
<220> FEATURE:
<223> OTHER INFORMATION: synthetic peptide

<400> SEQUENCE: 19

Lys Gly Arg Gln Val Lys Val Trp Phe Gln Asn Arg Arg Met Lys Trp
1               5                   10                  15

Lys Lys

<210> SEQ ID NO 20
<211> LENGTH: 35
<212> TYPE: PRT
<213> ORGANISM: Artificial Sequence
<220> FEATURE:
<223> OTHER INFORMATION: synthetic peptide

<400> SEQUENCE: 20

Phe Ile Gly Asn Leu Ala Leu Ser Asp Leu Leu Ala Gly Val Ala Tyr
1               5                   10                  15

Thr Ala Asn Leu Leu Leu Lys Lys Arg Thr Leu Arg Lys Asn Asp Arg
            20                  25                  30

Lys Lys Arg
        35
```

EXOSOME PRODUCTION METHOD

CROSS-REFERENCE TO RELATED APPLICATIONS

The present application claims the benefit of the foreign priority to Japanese Patent Application No. 2019-008474, filed Jan. 22, 2019, which is herein incorporated by reference in its entirety.

TECHNICAL FIELD

The present invention relates a method of producing exosomes. More particularly, the present invention relates to a method of producing induced lightweight exosomes in which the amount of proteins contained therein has been reduced by supplying a synthetic peptide disclosed herein to exosome-producing cells (cultured cells).

TECHNICAL BACKGROUND

Exosomes are membrane vesicles having a diameter of about 20 nm to 200 nm that are known to be secreted from various cells in the body or cultured cells. The interior thereof (namely, the lumen portion) as well as the membrane structure portion that composes the exosome contains various proteins, and the function of exosomes is known to diversify according to the types of these proteins.

In recent years, research has been proceeding on the application of exosomes to the medical field (such as research relating to drug delivery technology using exosomes as carriers). One example of this is technology relating to a method of forming exosomes from cells (such as cells isolated from tissue). More specifically, Japanese Patent Application Publication No. 2018-64550 discloses a method of forming artificial exosomes by bringing isolated stem cells into contact with prostaglandin E receptor-4 (EP4) antagonist.

In the case of attempting to apply exosomes to the medical field, there are cases in which technology is required to alter the amount of proteins contained in those exosomes depending on their application. For example, in the case of examining the use of exosomes as drug delivery carriers, it is preferable that substances other than the target drug or other introduced substance not be present, or be present in as low amount as possible, in the exosome to serve as a carrier. Consequently, technology is required for preliminarily reducing the amount of native protein present in the exosome to serve as a carrier. However, it has been difficult for conventional technology to easily and reliably reduce the amount of native protein present in exosomes produced during the production of exosomes serving as carriers.

Therefore, the present invention was created in order to solve the above-mentioned problems in the case of using exosomes as drug delivery carriers, and an object thereof is to provide a method of producing exosomes from prescribed cultured cells that is able to provide induced lightweight exosomes (iLE) in which the content of native protein present in the exosomes (namely, miscellaneous proteins capable of inherently being present) has been preliminarily reduced. In addition, another object of the present invention is to provide induced lightweight exosomes (iLE) produced according to this production method.

SUMMARY OF THE INVENTION

The inventor of the present invention focused on the transmembrane (TM) region of sphingosine 1-phosphate receptor 1 (S1PR1), which is a seven transmembrane protein expressed in various biological species, and particularly in mammals. The inventor of the present invention surprisingly found that by treating prescribed cultured cells using a synthetic peptide combining the amino acid sequence composing the second TM region from the N-terminal of S1PR1 and the amino acid sequence (hereinafter, referred to as CPP sequence) functioning as a cell penetrating peptide (CPP), in addition to being able to increase the amount of exosomes produced in the cultured cells, the content of native protein present in the produced exosomes decreases, thereby leading to completion of the present invention.

The method of producing exosomes disclosed herein is a method of producing induced lightweight exosomes (iLE), including:

preparing a cell culture containing prescribed cultured cells;

supplying at least once an artificially produced synthetic peptide to the cell culture and culturing the cell culture for a prescribed interval; and obtaining exosomes produced by the cultured cells from the cell culture following the culturing.

Here, the synthetic peptide comprises both of the following amino acid sequences indicated in (1) and (2):

(1) an exosome-inducing peptide sequence consisting of an amino acid sequence composing the second transmembrane (TM) region from the N-terminal of sphingosine 1-phosphate receptor 1 (S1PR1) or an amino acid sequence modified by deletion, substitution, or addition of one, two or three amino acid residues in the amino acid sequence; and, (2) an amino acid sequence functioning as a cell penetrating peptide (CPP sequence); and has a total number of amino acid residues of 100 or less.

According to this production method, the number of exosomes produced in target cultured cells can be increased. Moreover, induced lightweight exosomes (iLE) can be preferably produced in which the average amount of protein per particle is less than a prescribed amount.

In a preferable aspect of the production method disclosed herein, the exosome-inducing peptide sequence is the amino acid sequence represented by SEQ ID NO: 1.

In addition, in another preferable aspect of the production method disclosed herein, the CPP sequence may be a polyarginine sequence (typically composed of 5 or more and 20 or less of arginine residues although not particularly limited thereto), an amino acid sequence represented by any of SEQ ID NOs: 2 to 19, or an amino acid sequence modified by deletion, substitution, or addition of one, two or three amino acid residues in the amino acid sequence.

In another preferable aspect of the production method disclosed herein, the CPP sequence (or modified amino acid sequence functioning as a CPP) is arranged directly adjacent to the N-terminal or C-terminal of the above-mentioned exosome-inducing peptide sequence, or with ten or less (preferably five or less, such as one or two) amino acid residues functioning as a linker.

In a particularly preferable aspect, the synthetic peptide has the amino acid sequence represented by SEQ ID NO: 20.

The iLE production method disclosed herein enables to provide a novel exosome production method by including the supply of the synthetic peptides.

In addition, in another preferable aspect of the production method disclosed herein, exosomes produced by the cultured cells are obtained by isolating from the cell culture as an exosome fraction by ultracentrifugation in the obtaining exosomes. According to this aspect, exosomes can be preferably obtained.

In another preferable aspect, the production method disclosed herein further includes, analyzing a total amount of protein in the exosome fraction subsequently to the obtaining exosomes. Here, an average amount of protein per exosome is obtained by using the total amount. An exosome including the average amount of protein per exosome under a prescribed amount is determined as an induced lightweight exosome (iLE).

More preferably, the average amount of protein per particle of the exosomes is less than $8 \times 10^{-8}$ pg.

According to this production method, produced exosomes can be easily judged to be induced lightweight exosomes (iLE).

DESCRIPTION OF THE RELATED EMBODIMENTS

Figure 1:
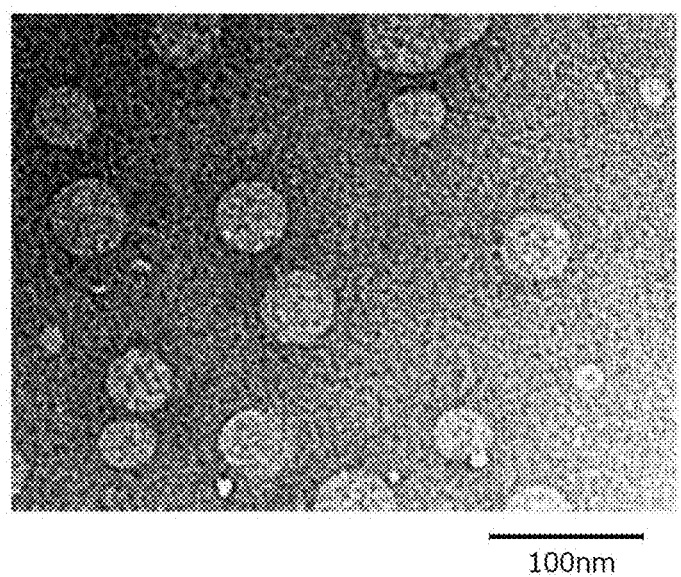
FIG. 1 is an electron micrograph of exosomes obtained from cultured cells (HeLa cells) treated with a sample peptide of an example.

The following provides an explanation of preferred embodiments of the present invention. Those matters required for carrying out the present invention (such as methods used to chemically synthesize peptides or general matters like those relating to cell culturing methods) other than matters not specifically mentioned in the present description (such as the primary structure or chain length of synthetic peptides) can be understood to be design matters of a person with ordinary skill in the art based on the prior art in fields such as cell engineering, physiology, medicine, pharmacology, organic chemistry, biochemistry, genetic engineering, protein engineering, molecule biology or genetics. The present invention can be carried out based on the contents disclosed in the present description and common general technical knowledge in the art. Furthermore, in the following explanation, amino acids are represented using single letter notation (but using three-letter notation in the case of the sequence listings).

The contents of literature cited in the present description are incorporated by reference in the present description in their entirety.

In the present description, "exosomes" refer to vesicles formed by a lipid bilayer that are secreted from various eukaryotic cells outside the cells. Although exosomes are typically vesicles having a diameter of about 20 nm to 200 nm, they are only required to be exosomes produced by target cultured cells and there are no particular limitations on the size or morphology thereof.

In addition, "induced lightweight exosomes (iLE)" refer to exosomes for which production has been artificially induced by supplying a synthetic peptide disclosed herein to target cultured cells, and are relatively lightweight exosomes (iLE) in which the content of native protein (namely, miscellaneous protein capable of being inherently present in exosomes normally produced by the target cultured cells) is reduced in comparison with exosomes normally produced by the target cultured cells when not supplied with the synthetic peptide.

In addition, in the present description, "cultured cells" refer to ordinary cells cultured in vitro (outside the body) and are not limited to a specific commercially established cell line. Cells contained in a culture (such as a primary culture) in the case of having cultured in vitro cells, tissue or organs that have been extracted from the body of a human or non-human biological species (and particularly mammals) are included in "cultured cells". Cells composing commercially established such as various tumor cells are typical examples of the "cultured cells" referred to here.

Furthermore, "tumor cells" have the same meaning as "cancer cells" and refer to cells that form various tumors that have reached the state of abnormal growth unrelated to surrounding normal tissue (so-called cancerous cells). "Cultured tumor cells" derived from cells composing various types of tumor cells (such as neuroblastoma or retinoblastoma), lymphoma or melanoma and the like are a preferable example of the "cultured cells" referred to here.

In addition, in the present description, a "synthetic peptide" refers to a peptide fragment that is capable of being stably present in a prescribed composition and is produced by artificial chemical synthetic or biosynthesis (namely, production based on genetic engineering) instead of only the peptide chains thereof being independently present and stable in nature. Here, a "peptide" is a term indicating an amino acid polymer having a plurality of peptide bonds, and although not limited by the total number of amino acid residues contained in the peptide chain, typically has a comparatively low molecular weight such that the total number of amino acid residues is 100 or less (and preferably 90 or less, more preferably 80 or less and particularly preferably 70 or less).

In addition, in the present description, an "amino acid residue" is a term that includes the N-terminal amino acid and C-terminal amino acid of a peptide chain unless specifically indicated otherwise.

Furthermore, the amino acid sequences described in the present description always have the N-terminal on the left side and the C-terminal on the right side.

In the present description, a "modified amino acid sequence" refers to an amino acid sequence formed by substituting, deleting or adding (inserting) from one to a plurality (typically nine or less and preferably five or less) of amino acid residues, such as one, two or three amino acid residues, with respect to a prescribed amino acid sequence without losing the function possessed by that prescribed amino acid sequence (such as exosome inducibility or cell membrane penetration performance). For example, a sequence formed by so-called conservative amino acid replacement, in which, one, two or three amino acid residues have been conservatively replaced (such as a sequence in which a basic amino acid residue has been replaced with another basic amino acid residue such as the mutual replacement of a lysine residue and arginine residue), or a sequence in which one, two or three amino acid residues have been added (inserted) with respect to a prescribed amino acid sequence, is a typical example of an amino acid sequence included in the modified amino acid sequence as referred to in the present description. Thus, in addition to synthetic peptides composed of the same amino acid sequence as an amino acid sequence of each of the sequence numbers, synthetic peptides comprised of a modified amino acid sequence obtained by substituting (such as the above-mentioned conservative amino acid replacement), deleting or adding one, two or three amino acid residues in an amino acid sequence of each of the sequence numbers, which similarly demonstrate exosome inducibility, are included in the peptides having exosome inducibility used in the induced lightweight exosome production method disclosed herein.

The production method disclosed herein is characterized by supplying an artificially produced synthetic peptide to a cell culture containing target cultured cells in vitro. In other words, the production method disclosed herein includes a step for preparing a cell culture containing target cultured cells (to be referred to as the "preparation step"), a step for supplying at least once a synthetic peptide containing an artificially produced prescribed exosome-inducing peptide sequence and a CPP sequence (the synthetic peptide is referred to as an "iLE-inducing synthetic peptide") to the target cell culture followed by culturing the cell culture for a prescribed interval (to be referred to as the "culturing step"), and a step for obtaining exosomes produced by the cultured cells after culturing (to be referred to as the "obtaining step").

The target cells and materials composing the medium for the cells (cultured cells) are contained in the cell culture prepared in the preparation step.

Examples of cultured cells include routinely available (and typically commercially available) cell lines such as tumor cell lines derived from humans or non-human mammals. For example, tumor cells such as uterine cancer, ovarian cancer or breast cancer cells can be used, and HeLa cells derived from human cervical cancer cells can be used preferably.

Materials composing the medium of the cultured cells comply with the conventionally recommended medium composition corresponding to the cultured cells, and there are no particular limitations thereon when carrying out the present invention. For example, medium can be used that has been prepared by adding serum such as fetal bovine serum (FBS), and components such as antibiotics as necessary, to commercially available media such as a-MEM, DMEM or MEM. Here, a serum-containing medium without serum-derived animal native exosomes may be used preferably from the viewpoint of obtaining induced lightweight exosomes (iLE) of high purity.

Next, in the culturing step, the iLE-inducing synthetic peptide is supplied at least once to the cell culture used followed by culturing the cell culture for a prescribed interval.

The method used to supply the iLE-inducing synthetic peptide to the cultured cells may include adding an effective suitable amount of the iLE-inducing synthetic peptide at any stage of the culturing step (such as simultaneous to the start of culturing, during the initial stage after the start of culturing or after culturing (growing) or subculturing for a prescribed interval).

There are no particular limitations on the amount added or number of additions since they can vary according to conditions such as the species and morphology of cultured cells (such as whether an ordinary cell line is used or whether harvested tissue or other primary culture is used), cell density (cell density at the start of culturing), number of subculturing, culturing conditions or type of medium. The effective amount is preferably such that the iLE-inducing synthetic peptide is added once or twice or more times so that the concentration of iLE-inducing synthetic peptide in the medium is within the range of roughly 0.5 µM to 40 µM and preferably within the range of 1 µM to 20 µM (for example, 2.5 µM to 10 µM).

Although there are no particular limitations thereon, the culturing period is preferably a culturing period of about two days to five days in a $CO_2$-rich environment (such as a $CO_2$ concentration of about 5%) under temperature conditions of about 37° C. from the viewpoint of efficiently obtaining an adequate amount of induced lightweight exosomes (iLE) with few contaminants.

The iLE-inducing synthetic peptide is a short-chain synthetic peptide not present in nature that was discovered by the present inventor to increase production of exosomes in cultured cells (as well as have iLE inducibility), and is characterized by being provided with both of the previously described two amino acid sequences, namely:

(1) an exosome-inducing peptide sequence made up with an amino acid sequence in the second TM region from the N-terminal of S1PR1 (hereinafter, also referred to as "S1PR1-TM2 sequence") or an amino acid sequence modified by deletion, substitution, or addition of one, two or three amino acid residues in the amino acid sequence; and, (2) an amino acid sequence functioning as a cell penetrating peptide (CPP sequence).

S1PR1 is typically a G-protein conjugated receptor protein composed of about 382 amino acid residues that is involved in the proliferation and motility of cancer cells by coupling with SW (refer to Sphingosine 1-phosphate and Cancer, Nigel J. Pyne and Susan Pyne, Nature Reviews, 10, 489-503 (2010)).

However, the S1PR1-TM2 sequence had not been found to have exosome inducibility. A synthetic protein was obtained that was artificially produced by synthesizing the S1PR1-TM2 sequence and adding CPP to that sequence, and the findings obtained as a result of using that synthetic peptide of increased production of exosomes in cultured cells (namely, exosome inducibility) and the produced exosomes consisting mainly of induced lightweight exosomes (iLE) having a reduced content of native protein contained therein were completely unexpected at the time of filing of the present application.

The gene encoding S1PR1 (including cDNA) is found in mammals such as humans, mice, rats, cows, cats or rhesus monkeys as well as in birds such as chickens. S1PR1 gene data and amino acid sequence data can be acquired by accessing the knowledge bases (databases) of various public international institutions. For example, total amino acid sequence data and amino acid sequence data of the TM region of S1PR1 derived from various biological species can be acquired from Universal Protein Resource (UniProt).

The S1PR1-TM2 sequence is shown in SEQ ID NO: 1. More specifically, this sequence is a sequence derived from humans, mice, rats, cows, cats and rhesus monkeys. The S1PR1-TM2 sequence is shared by all of these animal species.

Various conventionally known CPP can be used for the CPP sequence. For example, so-called polyarginine (Rn), which is comprised of 3 or more, preferably 5 or more and 20 or less, and more preferably 9 or less arginine residues, is preferable for the CPP sequence used here. Various other known CPPs can be used.

Although there are no particular limitations thereon, preferable examples of CPPs are shown in SEQ ID NOs: 2 to 19. More specifically, these sequences are as indicated below.

The amino acid sequence of SEQ ID NO: 2 corresponds to a nucleolar localization signal (NoLS) consisting of a total of 14 amino acid residues derived from basic fibroblast growth factor (FGF-2).

The amino acid sequence of SEQ ID NO: 3 corresponds to a NoLS consisting of a total of 18 amino acid residues derived from a type of nucleolar protein (ApLLP).

The amino acid sequence of SEQ ID NO: 4 corresponds to a NoLS consisting of a total of 16 amino acid residues derived from herpes simplex virus type 1 (HSV-1) protein (γ(1)34.5).

The amino acid sequence of SEQ ID NO: 5 corresponds to a NoLS consisting of a total of 19 amino acid residues derived from the p40 protein of human I-mfa domain-containing protein (HIC).

The amino acid sequence of SEQ ID NO: 6 corresponds to a NoLS consisting of a total of 16 amino acid residues derived from the MEQ protein of Marek's disease virus (MDV).

The amino acid sequence of SEQ ID NO: 7 corresponds to a NoLS consisting of a total of 17 amino acid residues derived from Survivin-deltaEx3, which is a protein that inhibits apoptosis.

The amino acid sequence of SEQ ID NO: 8 corresponds to a NoLS consisting of a total of 7 amino acid residues derived of the vascular growth factor, angiogenin.

The amino acid sequence of SEQ ID NO: 9 corresponds to a NoLS consisting of a total of 8 amino acid residues derived from the nuclear phosphoprotein, MDM2 that forms a complex with p53 tumor suppressor protein.

The amino acid sequence of SEQ ID NO: 10 corresponds to a NoLS consisting of a total of 9 amino acid residues derived from GGNNVa, which is a betanodavirus protein.

The amino acid sequence of SEQ ID NO: 11 corresponds to a NoLS consisting of a total of 7 amino acid residues derived from NF-KB-inducing kinase (NIK).

The amino acid sequence of SEQ ID NO: 12 corresponds to a NoLS consisting of a total of 15 amino acid residues derived from nuclear VCP-like protein.

The amino acid sequence of SEQ ID NO: 13 corresponds to a NoLS consisting of a total of 18 amino acid residues derived from the nucleolar protein, p120.

The amino acid sequence of SEQ ID NO: 14 corresponds to a NoLS consisting of a total of 14 amino acid residues derived from the ORF57 protein of herpes virus saimiri (HVS).

The amino acid sequence of SEQ ID NO: 15 corresponds to a NoLS consisting of a total of 13 amino acid residues from the 491st amino acid residue to the 503rd amino acid residue of LIM kinase 2 present in human endothelial cells, which is a type of protein kinase involved in intracellular signal transduction.

The amino acid sequence of SEQ ID NO: 16 corresponds to a NoLS consisting of a total of 8 amino acid residues contained in the nucleocapsid protein (N protein) of avian infectious bronchitis virus (IBV).

The amino acid sequence of SEQ ID NO: 17 corresponds to a membrane-penetrating motif consisting of a total of 9 amino acid residues derived from the protein transduction domain contained in TAT of human immunodeficiency virus (HIV).

The amino acid sequence of SEQ ID NO: 18 corresponds to a membrane-penetrating motif consisting of a total of 11 amino acid residues of a protein transduction domain in which the above-mentioned TAT has been modified (PTD4).

The amino acid sequence of SEQ ID NO: 19 corresponds to a membrane-penetrating motif consisting of a total of 18 amino acid residues derived from ANT of Antennapedia, which is a mutant of Drosophila.

Among these sequences, those amino sequences associated with NoLS and TAT (or modified amino acid sequences thereof) are particularly preferable. For example, the NoLS-associated CPP sequences as indicated in SEQ ID NO: 15 and SEQ ID NO: 16 or the TAT- or ANT-associated CPP sequences of SEQ ID NOs: 17 to 19 can be used preferably.

As previously described, the peptide chain (amino acid sequence) of the iLE-inducing synthetic peptide is provided with:

(1) an exosome-inducing peptide sequence, and (2) a CPP sequence, and either the exosome-inductincg peptide sequence or CPP sequence may be relatively arranged on the N-terminal side (C-terminal side).

The exosome-inducing peptide sequence and the CPP sequence are preferably arranged to be substantially adjacent, and more specifically, the CPP sequence, for example, is preferably arranged directly on the N-terminal side or C-terminal side of the exosome-inducing peptide sequence. Alternatively, the total number of amino acid residues functioning as a linker that links the two sequences preferably consists of ten amino acid residues or less (and more preferably five or less, such as one or two amino acid residues).

The iLE-inducing synthetic peptide can contain a sequence moiety (amino acid residues) other than an amino acid sequence composing the exosome-inducing peptide sequence and CPP sequence provided exosome inducibility is not lost.

The total number of amino acid residues composing the peptide chain of the synthetic peptide may suitably be 100 or less, preferably 80 or less and more preferably 70 or less (such as a peptide chain of about 30 amino acid residues to 50 amino acid residues). A peptide having a short chain length in this manner is easily chemically synthesized and is easily to be synthesized. Although there are no particular limitations thereon, a linear or helical chain may be preferable from the viewpoint of being difficult to function as an immunogen (antigen). It is difficult for this form of peptide to compose an epitope.

Although there are no particular limitations on the proportion of the exosome-inducing peptide sequence in the amino acid sequences of the entire synthetic peptide and CPP sequence as long as exosome-inducing properties are not lost, the proportion thereof may preferably be about 80% by number or more and more preferably 90% by number or more. Furthermore, although it may be preferable that all of the amino acid residues are L amino acids, a portion or all of the amino acid residues may be substituted with D amino acids and non-natural artificially synthesized amino acids provided exosome inducibility is not lost.

At least one amino acid residue of the synthetic peptide may preferably be amidated. Amidation of the carboxyl group of an amino acid residue (and typically the C-terminal amino acid residue of the peptide chain) makes it possible to improve structural stability of the synthetic peptide (in terms of, for example, protease resistance). For example, when the CPP sequence moiety composes the C-terminal of the exosome-inducing peptide, the C-terminal amino acid residue of that sequence moiety may preferably be amidated. Meanwhile, when the exosome-inducing peptide sequence moiety composes the C-terminal of the synthetic peptide, the C-terminal amino acid residue of that sequence moiety may preferably be amidated. In another preferable aspect, stability of the synthetic peptide can be improved by amidating the C-terminal amino acid residue of the synthetic peptide having the amino acid sequence of SEQ ID NO: 20.

The synthetic peptide can be easily synthesized in compliance with ordinary chemical synthesis methods. For example, conventionally known solid phase synthesis or liquid phase synthesis may be employed. Solid phase synthesis applying t-butyloxycarbonyl (Boc) or 9-fluorenyl-methoxycarbonyl (Fmoc) as an amino acid protecting group is preferable.

The peptide chain of the synthetic peptide can be synthesized to have a desired amino acid moiety and modified moiety (such as amidation of the C-terminal) by solid phase synthesis using a commercially available peptide synthesizer.

Alternatively, the synthetic peptide may be synthesized by employing a genetic engineering technique and the like. Since the method used per se does not particularly characterize the present invention, a detailed explanation thereof is omitted.

The obtaining step includes a step for obtaining exosomes produced by cultured cells after culturing. More specifically, exosomes produced by cultured cells can be obtained by isolating from a culture of the cultured cells as exosome fractions by any of the methods described below.

A conventionally known method can be used to obtained exosomes from a culture broth. For example, exosomes can be isolated and collected by a conventionally frequently practiced ultracentrifugation method (see, for example, Thery C., Curr. Protoc. Cell Biol. (2006) Chapter 3: Unit 3.22).

Alternatively, exosomes can be obtained from a culture broth by a method such as immunoprecipitation, FACS, ultrafiltration, gel filtration, filtration, HPLC or adsorption onto a polymer or beads. Exosome may also be obtained using a commercially available exosome isolation reagent (kit). For example, desired exosomes can be obtained by purchasing and using, for example, the exosome isolation kit sold by Cosmo Bio Co., Ltd.

An ultracentrifugation method can be used preferably. According to this method, overall exosomes can be obtained more reliably by preventing outflow of specific components (that can make collection difficult). Although there are no particular limitations thereon, contaminants can be removed by pretreatment in the form of centrifugal separation in several times at a centrifugal force of, such as, about 300×g to 10,000×g (such as 300x g for 5 minutes to 20 minutes, 2,000×g for 5 minutes to 20 minutes and 10,000×g for 20 minutes to 40 minutes under conditions of 4° C.) followed by carrying out ultracentrifugation once, twice or three times at a centrifugal force of about 100,000×g to 200,000×g for about 60 minutes to 90 minutes (such as by carrying out ultracentrifugation twice at 110,000×g for 60 minutes to 90 minutes under conditions of 4° C.) to be able to obtain highly pure exosomes with few contaminants.

Obtaining exosomes with the methods (such as ultracentrifugation) can be confirmed by, for example, observation using a transmission electron microscope (and typically by negative staining), or by detecting an exosome marker protein (such as CD9, CD63 or CD81) by a method such as western blotting, ELISA or FACS (typically, immunological method). In addition, exosome RNA may also be measured.

The number of exosomes in an exosome fraction can preferably be determined by measuring the number of exosome particles N (number/mL) present in the exosome fraction using a commercially available nanoparticle analyzer. More specifically, NanoSight LM10 (Malvern Panalytical Ltd.), for example, can be used preferably.

The production method disclosed herein preferably further includes a step for analyzing the total amount of protein in the exosome fraction (to be referred to as the "analyzing step") after the obtaining step.

More specifically, the analyzing step preferably includes, for example, measurement of the total of amount of protein P (μg/mL) contained in the exosome fraction. A conventionally known method (such as BCA assay) can be used without any particular limitations to measure the amount of proteins. As a result, the average amount of protein per exosome, EP (μg), can be calculated based on the following equation (1).

$$EP \times P/N \qquad (1)$$

Here, exosomes contained in the exosome fraction in which the average amount of protein per exosome is less than $8 \times 10^{-8}$ μg can be judged to be induced lightweight exosome xosomes (iLE).

Exosome production in cultured cells can be increased by the exosome production method disclosed herein. Moreover, the exosomes can be induced lightweight exosomes (iLE) in which the average amount of protein per exosome is less than a prescribed amount. Induced lightweight exosomes (iLE) can be function as, for example, preferable carrier materials (such as drug carrier materials). Thus, the exosome production method disclosed herein can be preferably used in research relating to drug delivery technology.

Although the following provides an explanation of several examples relating to the present invention, the examples are not intended to limit the present invention to that indicated therein.

TEST EXAMPLE 1

Sample Peptide Synthesis

The sample peptide indicated in Table 1 was produced using a commercially available peptide synthesizer. More specifically, a synthetic peptide containing the amino acid sequence of SEQ ID NO: 15 (NoLS of LIM kinase 2) as a CPP sequence on the C-terminal of the amino acid sequence of the second TM region from the N-terminal of human S1PR1 (SEQ ID NO: 1) was produced as sample peptide (SEQ ID NO: 20).

TABLE 1

| Amino acid sequence | Number of amino acid residues | SEQ ID NO |
|---|---|---|
| FIGNLALSDLLAGVAYTANLLL KKRTLRKNDRKKR-CONH$_2$ | 35 | 20 |

The above-mentioned sample peptide was synthesized by carrying out solid phase synthesis (Fmoc method) using a commercially available peptide synthesizer in accordance with the manual. Furthermore, since the manner per se in which the peptide synthesizer was used does not characterize the present invention, a detailed explanation thereof is omitted. Furthermore, the carboxyl group (—COOH) of the C-terminal amino acid of the sample peptide shown in Table 1 is amidated (—CONH$_2$) in the peptide having the amino acid sequence of that SEQ ID NO.

The synthesized sample peptide was dissolved in dimethylsulfoxide (DMSO) to prepare a stock solution of the sample peptide (concentration: 2.5 mM).

TEST EXAMPLE 2

Exosome Production and Collection

The exosomes of the Example, Comparative Example 1 and Comparative Example 2 were produced and obtained according to the process explained below.

EXAMPLE

More specifically, a currently commercially available human cervical cancer cell line (HeLa cells) was used as the test cultured cells.

α-MEM medium containing 10% FBS (product of Gibco) was used to culture the HeLa cells. Furthermore, FBS free of native exosomes derived from animal serum was used for the FBS.

The details of Test Example 2 are as described below.

A suitable amount of medium containing FBS at a concentration of 10% was placed in cell culture dishes having a diameter of 100 mm followed by seeding with HeLa cells so that the number of cells per dish was about $2 \times 10^6$ cells.

Next, the cells were cultured in a-MEM medium containing 10% FBS having the sample peptide suspended therein at a concentration of 5 μM under conditions of 5% $CO_2$ at 37° C. for 48 hours.

Subsequently, the culture broth was obtained and subjected to ultracentrifugation to isolate and recover the exosomes. More specifically, centrifugation was carried out continuously as described below under conditions of 4° C. Namely, the obtained culture broth was centrifuged for 10 minutes at 300×g followed by obtaining the supernatant and subjecting to ultracentrifugation for 10 minutes at 2,000×g. The supernatant was obtained and centrifugation was carried out for 30 minutes at 10,000×g (pretreatment). The supernatant was again recovered and ultracentrifugation was carried out twice for 70 minutes at 110,000×g.

Following the ultracentrifugation, the precipitate was suspended in phosphate-buffered saline (PBS). As a result of the treatment, an exosome fraction derived from the HeLa cells was obtained.

Comparative Example 1

The exosome fraction of Comparative Example 1 was obtained using the same process as that of the Example with the exception of culturing the HeLa cells in a-MEM medium containing 10% FBS having a conventionally known sphingosine kinase inhibitor suspended therein at a concentration of 5 μM.

Comparative Example 2

The exosome fraction of Comparative Example 2 was obtained using the same process as that of the Example with the exception of culturing the HeLa cells in a-MEM medium containing 10% FBS.

TEST EXAMPLE 3

Exosome Observation

The exosomes of the example were observed using a transmission electron microscope (TEM). A TEM micrograph of exosomes of the example is shown in FIG. 1 as a typical example of the results.

TEST EXAMPLE 4

Calculation of Number of Exosomes

The number of exosomes was calculated for each of the three exosome fractions produced as described above. More specifically, the numbers of exosome particles in the exosome fractions were counted followed by calculating the number of exosomes using NanoSight LM10 (Malvern Panalytical Ltd.).

Figure 2:
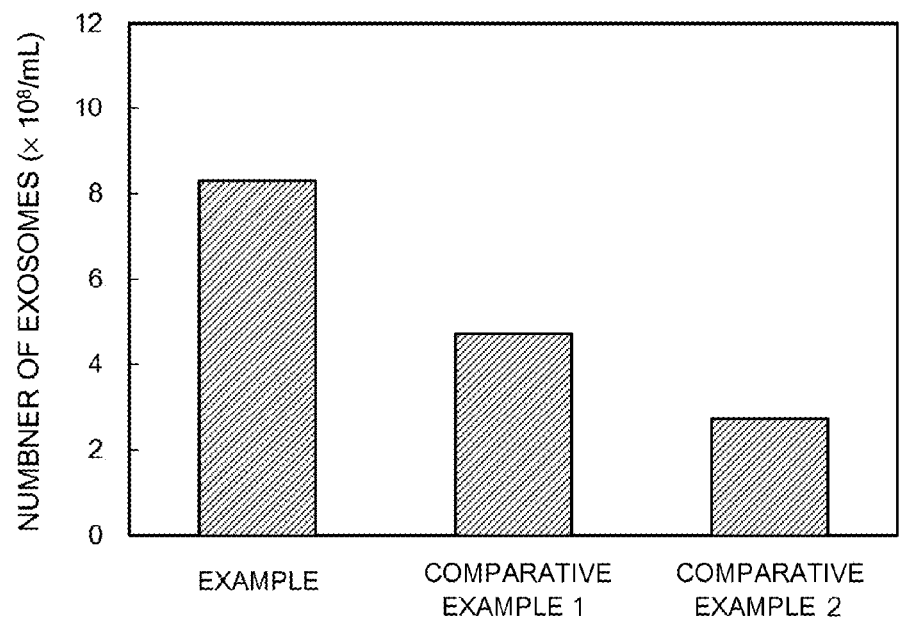
FIG. 2 is a graph indicating the number of exosomes contained per 1 mL of exosome fractions recovered in a test example.

The results are shown in Table 2 and FIG. 2.

TABLE 2

| Exosome concentration ($\times 10^8$/mL) | |
| --- | --- |
| Example | 8.31 |
| Comparative Example 1 | 4.72 |
| Comparative Example 2 | 2.74 |

As is clear from Table 2 and FIG. 2, the number of exosomes was confirmed to increase considerably as a result of using the sample peptide.

TEXT EXAMPLE 5

Measurement of Amount of Protein

The amount of protein was measured for each of the three exosome fractions produced as described above. More specifically, total protein concentration in the exosome fractions was obtained using the Pierce™ BCA Protein Assay Kit (Thermo Fisher Scientific) followed by obtaining the amount of proteins per particle according to equation (1).

Figure 3:
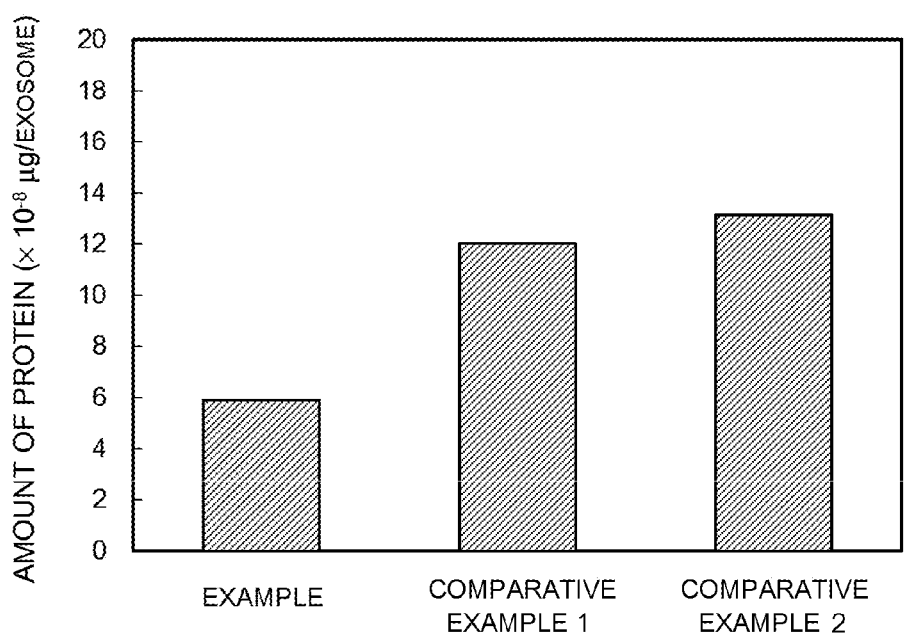
FIG. 3 is a graph indicating the average amount of protein per exosome particle contained in exosome fractions obtained in a test example.

The results are shown in Table 3 and FIG. 3.

TABLE 3

| Amount of protein ($\times 10^{-8}$ μg/exosome) | |
| --- | --- |
| Example | 5.9 |
| Comparative Example 1 | 12.0 |
| Comparative Example 2 | 13.1 |

As is clear from Table 3 and FIG. 3, the amount of proteins in the exosomes of the Example decreased considerably in comparison with Comparative Example 1 and Comparative Example 2. Use of the above-mentioned sample peptide was confirmed to enable the production of exosomes in which the amount of proteins per particle was $8.0 \times 10^1$ μg or less (namely, iLE).

As has been previously described, according to the exosome production method disclosed herein, induced lightweight exosomes (namely iLE) can be produced in which the amount of proteins per exosome particle is $8.0 \times 10^{-8}$ μg or less. Consequently, use of the exosome production method provided by the present invention makes it possible to easily produce and supply induced lightweight exosomes (iLE) suitable for use as drug delivery carriers.

The invention claimed is:

1. A method of producing induced lightweight exosomes (iLE), comprising:
preparing a cell culture containing exosome-producing cells;
adding at least once an artificially produced synthetic peptide to the cell culture containing exosome-producing cells;
culturing the exosome-producing cells in the presence of the artificially produced synthetic peptide;
and obtaining exosomes produced by the exosome-producing cells from the cell culture following the culturing;
wherein the artificially produced synthetic peptide comprises:
(1) an exosome-inducing peptide consisting of the amino acid sequence of SEQ ID NO: 1; and,
(2) a cell penetrating peptide (CPP);
and wherein the artificially produced synthetic peptide is no more than 100 amino acids in length.

2. The method according to claim 1, wherein the CPP is selected from the group consisting of polyarginine and SEQ ID NOs: 2 to 19.

3. The method according to claim 1, wherein the CPP is directly connected to the N-terminus or C-terminus of the exosome-inducing peptide, or the CPP is connected to the exosome-inducing peptide via a linker that is no more than 10 amino acids in length.

4. The method according to claim 1, wherein the artificially produced synthetic peptide consists of the amino acid sequence of SEQ ID NO: 20.

5. The method according to claim 1, wherein the exosomes produced by the exosome-producing cells are obtained from the cell culture as an exosome fraction by ultracentrifugation.

6. The method according to claim 1, further comprising analyzing a total amount of protein in the exosome fraction after obtaining the exosomes; and obtaining an average amount of protein per exosome.

7. The method according to claim 6, wherein the average amount of protein per exosome is less than $8 \times 10^{-8}$ μg.

* * * * *